(12) United States Patent
Shambaugh et al.

(10) Patent No.: US 10,549,019 B2
(45) Date of Patent: *Feb. 4, 2020

(54) SINGLE-PIECE VOLUTE

(71) Applicant: HeartWare, Inc., Miami Lakes, FL (US)

(72) Inventors: Charles R. Shambaugh, Coral Gables, FL (US); Mustafa Ertan Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 102 days.

This patent is subject to a terminal disclaimer.

(21) Appl. No.: 15/795,436

(22) Filed: Oct. 27, 2017

(65) Prior Publication Data

US 2018/0117226 A1 May 3, 2018

Related U.S. Application Data

(60) Provisional application No. 62/414,270, filed on Oct. 28, 2016.

(51) Int. Cl.
*A61M 1/10* (2006.01)
*A61M 1/12* (2006.01)
(Continued)

(52) U.S. Cl.
CPC ........ *A61M 1/1036* (2014.02); *A61M 1/1012* (2014.02); *A61M 1/1017* (2014.02);
(Continued)

(58) Field of Classification Search
CPC ............................ A61M 1/101; A61M 1/1008
See application file for complete search history.

(56) References Cited

U.S. PATENT DOCUMENTS

| 7,972,122 B2 | 7/2011 | LaRose et al. |
| 8,007,254 B2 * | 8/2011 | LaRose ................. A61M 1/101 417/356 |
| 8,419,609 B2 | 4/2013 | Shambaugh, Jr. et al. |

FOREIGN PATENT DOCUMENTS

| EP | 1267959 B1 | 6/2005 |
| EP | 2774633 A1 | 10/2014 |

(Continued)

OTHER PUBLICATIONS

International Search Report and Written Opinion dated Jan. 30, 2018 for corresponding International Application No. PCT/US2017/05871; International Filing Date: Oct. 27, 2017consisting of 12-pages.

*Primary Examiner* — Alyssa M Alter
(74) *Attorney, Agent, or Firm* — Christopher & Weisberg, P.A.

(57) ABSTRACT

A blood pump casing including a unitary body. The unitary body defines an inlet chamber extending along a first axis and having a first radius perpendicular to the first axis. A transition chamber is connected to the inlet chamber and has a wall extending in a circumferential direction around the first axis, the wall has a major radius and a minor radius from the first axis, the major radius being greater than the first radius. A post extends from the transition chamber into the inlet chamber along the first axis, the post tapers in the direction around the first axis toward the inlet chamber. An outlet is connected to the transition chamber and extends along a second axis transverse to the first axis.

20 Claims, 10 Drawing Sheets

(51) Int. Cl.
*B33Y 80/00* (2015.01)
*B33Y 10/00* (2015.01)
*B29C 64/135* (2017.01)
*B29L 31/00* (2006.01)

(52) U.S. Cl.
CPC .............. *A61M 1/122* (2014.02); *B33Y 80/00* (2014.12); *A61M 2207/00* (2013.01); *B29C 64/135* (2017.08); *B29K 2995/0056* (2013.01); *B29L 2031/753* (2013.01); *B33Y 10/00* (2014.12)

(56) References Cited

FOREIGN PATENT DOCUMENTS

| | | |
|---|---|---|
| WO | 2012150045 A2 | 11/2012 |
| WO | 2014047516 A1 | 3/2014 |
| WO | 2017112698 A1 | 6/2017 |

* cited by examiner

SINGLE-PIECE VOLUTE

CROSS-REFERENCE TO RELATED APPLICATION

This application is related to and claims priority to U.S. Provisional Patent Application Ser. No. 62/414,270, filed Oct. 28, 2016, entitled SINGLE-PIECE VOLUTE, the entirety of which is incorporated herein by reference.

STATEMENT REGARDING FEDERALLY SPONSORED RESEARCH OR DEVELOPMENT n/a

TECHNICAL FIELD

The present invention relates to a pump casing, and in a particular to a pump casing for mechanical circulatory support devices or "MCSDs."

BACKGROUND

Pump casings are used to collect fluid induced by an impeller at an upstream location, and to channel this fluid to an outlet port located at a downstream location. Fluid flow path in pump casings are typically designed to convert dynamic energy (velocity) to pressure energy, i.e., to convert pump energy transmitted from the impeller to pressure energy.

Incorrectly sized and/or improperly manufactured casings may account for a significant portion of overall pump losses. Proper design of the fluid flow path in pump casings is critical to ensure overall pump performance and to minimize pump energy consumption. This is especially true for pumps used in MCSDs to assist the pumping action of the heart. Pump casings for MCSDs are generally volute-shaped with a cross-section of the volute (flow channel) increasing in a circumferential direction of the discharge in order to maintain a constant fluid velocity. The volute-shaped flow path is designed to maintain constant angular momentum (CAM) or a constant mean velocity (CMV).

Pump casings with intricate flow channels to achieve the desired flow characteristics have complex internal walls and do not easily lend themselves to fabrication by commonly used methods. Pump casings used in MCSDs are much smaller than pump casings used in most other applications in order to allow the MCSD to be implanted in a patient. The miniature scale of the MCSD pump casings further complicate the efforts to manufacture these pump casings by conventional methods. Pump casings of the size used in MCSDs are generally fabricated in two or more components which are attached to one another later. This further increases the effort of manufacturing these pump casings.

SUMMARY

The present invention advantageously provides a blood pump casing including a unitary body. The unitary body defines an inlet chamber extending along a first axis and having a first radius perpendicular to the first axis. A transition chamber is connected to the inlet chamber and has a wall extending in a circumferential direction around the first axis, the wall has a major radius and a minor radius from the first axis, the major radius being greater than the first radius. A post extends from the transition chamber into the inlet chamber along the first axis, the post tapers in the direction around the first axis toward the inlet chamber. An outlet is connected to the transition chamber and extends along a second axis transverse to the first axis.

In another aspect of this embodiment, the body includes a polymer.

In another aspect of this embodiment, the minor radius is equal to or greater than the first radius.

In another aspect of this embodiment, the post is conical.

In another aspect of this embodiment, the outlet includes an enclosed channel having a first segment with a substantially rectangular cross-section transverse to the second axis in communication with the transition chamber, and a second segment with a substantially circular cross-section transverse to the second axis in communication with the first segment.

In another aspect of this embodiment, the first axis is perpendicular to the second axis.

In another aspect of this embodiment, the body includes an inner first wall surrounding the inlet chamber over at least a portion of the axial extent of the inlet chamber and an outer second wall surrounding the first wall, the first and second walls defining an annular space.

In another aspect of this embodiment, the inlet chamber is cylindrical.

In another embodiment, a mechanical circulatory support device includes a unitary body. The unitary body defines an inlet chamber extending along a first axis and having a first radius perpendicular to the first axis. A transition chamber is connected to the inlet chamber and has a wall extending in a circumferential direction around the first axis, the wall has a major radius and a minor radius from the first axis, the major radius being greater than the first radius. A post extends from the transition chamber into the inlet chamber along the first axis, the post tapers in the direction around the first axis toward the inlet chamber. An outlet is connected to the transition chamber and extends along a second axis transverse to the first axis. A housing is connected to the inlet chamber and a rotor is disposed within the housing and configured to impel blood into the inlet chamber.

In another aspect of this embodiment, the post is conical.

In another aspect of this embodiment, the outlet includes an enclosed channel having a first segment with a substantially rectangular cross-section transverse to the second axis in communication with the transition chamber, and a second segment with a substantially circular cross-section transverse to the second axis in communication with the first segment.

In another aspect of this embodiment, the first axis is perpendicular to the second axis.

In another aspect of this embodiment, the body includes an inner first wall surrounding the inlet chamber over at least a portion of the axial extent of the inlet chamber and an outer second wall surrounding the first wall, the first and second walls defining an annular space.

In another aspect of this embodiment, the inlet chamber is cylindrical.

In another embodiment, a method of fabricating a blood pump casing includes forming the body of the blood pump casing by an additive manufacturing process, the body of the casing being unitary. The unitary body defines an inlet chamber extending along a first axis and having a first radius perpendicular to the first axis. A transition chamber is connected to the inlet chamber and has a wall extending in a circumferential direction around the first axis, the wall has a major radius and a minor radius from the first axis, the major radius being greater than the first radius. A post extends from the transition chamber into the inlet chamber along the first axis, the post tapers in the direction around the first axis toward the inlet chamber. An outlet is connected to the transition chamber and extends along a second axis transverse to the first axis.

In another aspect of this embodiment, the additive manufacturing process includes stereolithography.

In another aspect of this embodiment, the body of the casing is made of a resin polymer.

In another aspect of this embodiment, the additive manufacturing process includes fused deposition modeling.

In another aspect of this embodiment, the additive manufacturing process includes inkjet printing.

In another aspect of this embodiment, the additive manufacturing process includes powder bed techniques.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Referring now to the drawings in which like reference designators refer to like elements, there is shown in FIGS. 1-8, a pump casing according to one embodiment of the invention and designated generally as "100." The pump casing 100 has a monolithic, i.e unitary, body defining an inlet chamber 102, a transition chamber 104, and an outlet 106. Inlet chamber 102 and transition chamber 104 are connected to each other and are disposed around a first longitudinal axis L1. Outlet 104 extends around a second axis L2, which is perpendicular to first axis L1. A post 114 (best seen in FIG. 4) which may be conical or any shape, extends from the base of the transition chamber 104 into the inlet chamber 102 along longitudinal axis L1.

Figure 1:
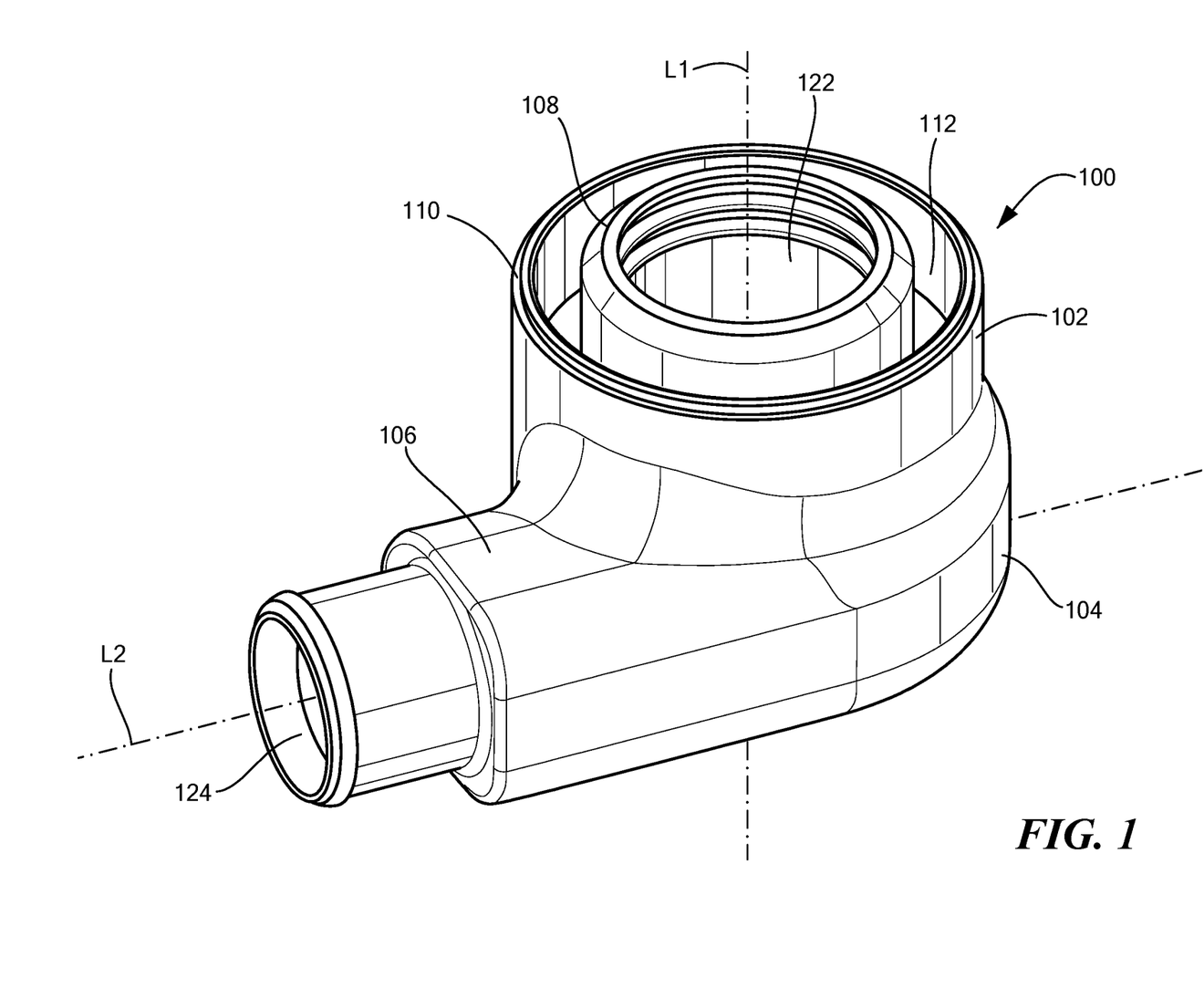
FIG. 1 is a perspective view of a pump casing according to one embodiment of the present disclosure.
Figure 2:
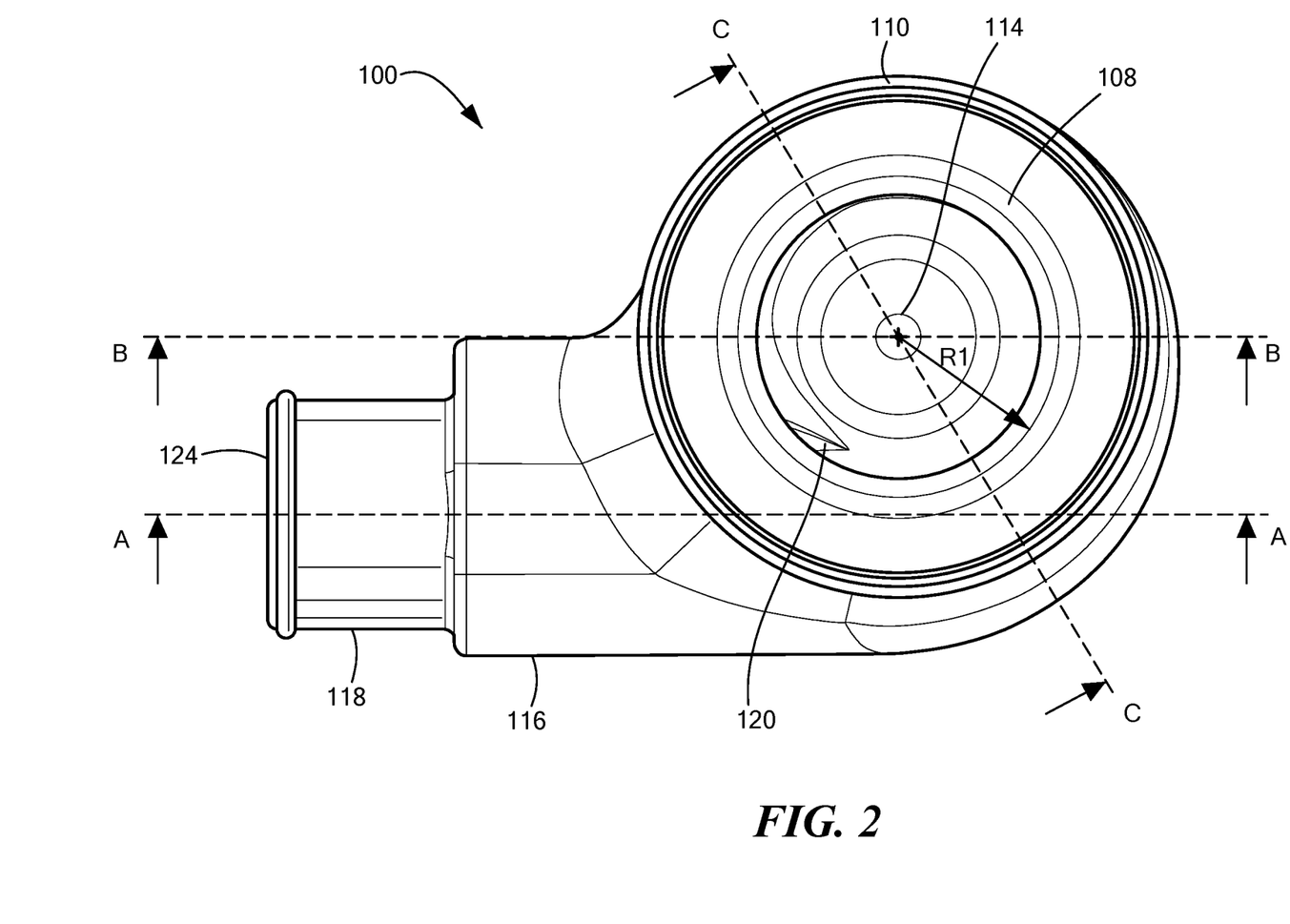
FIG. 2 is a top view of the pump casing of FIG. 1.
Figure 3:
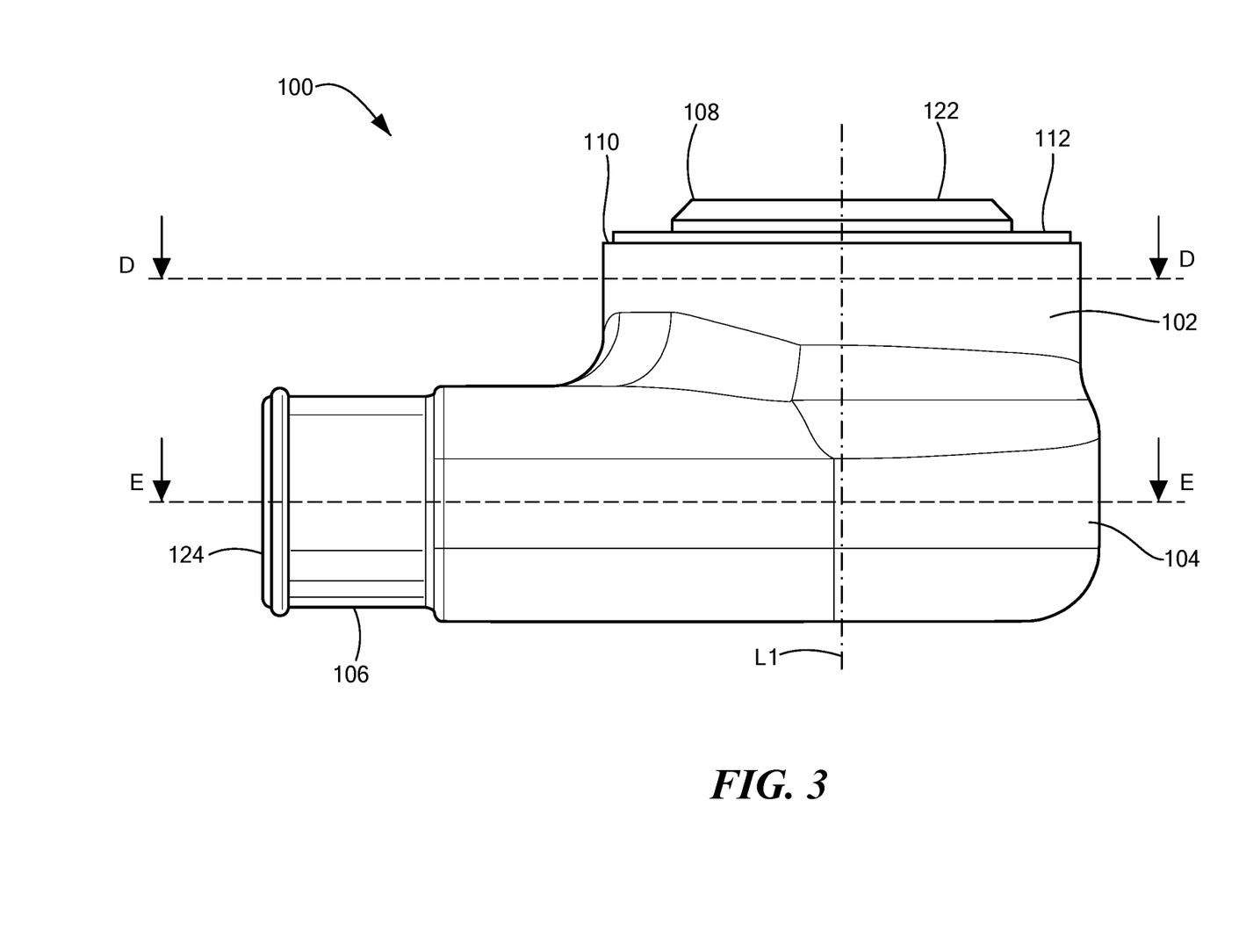
FIG. 3 is a side view of the pump casing of FIG. 1.
Figure 4:
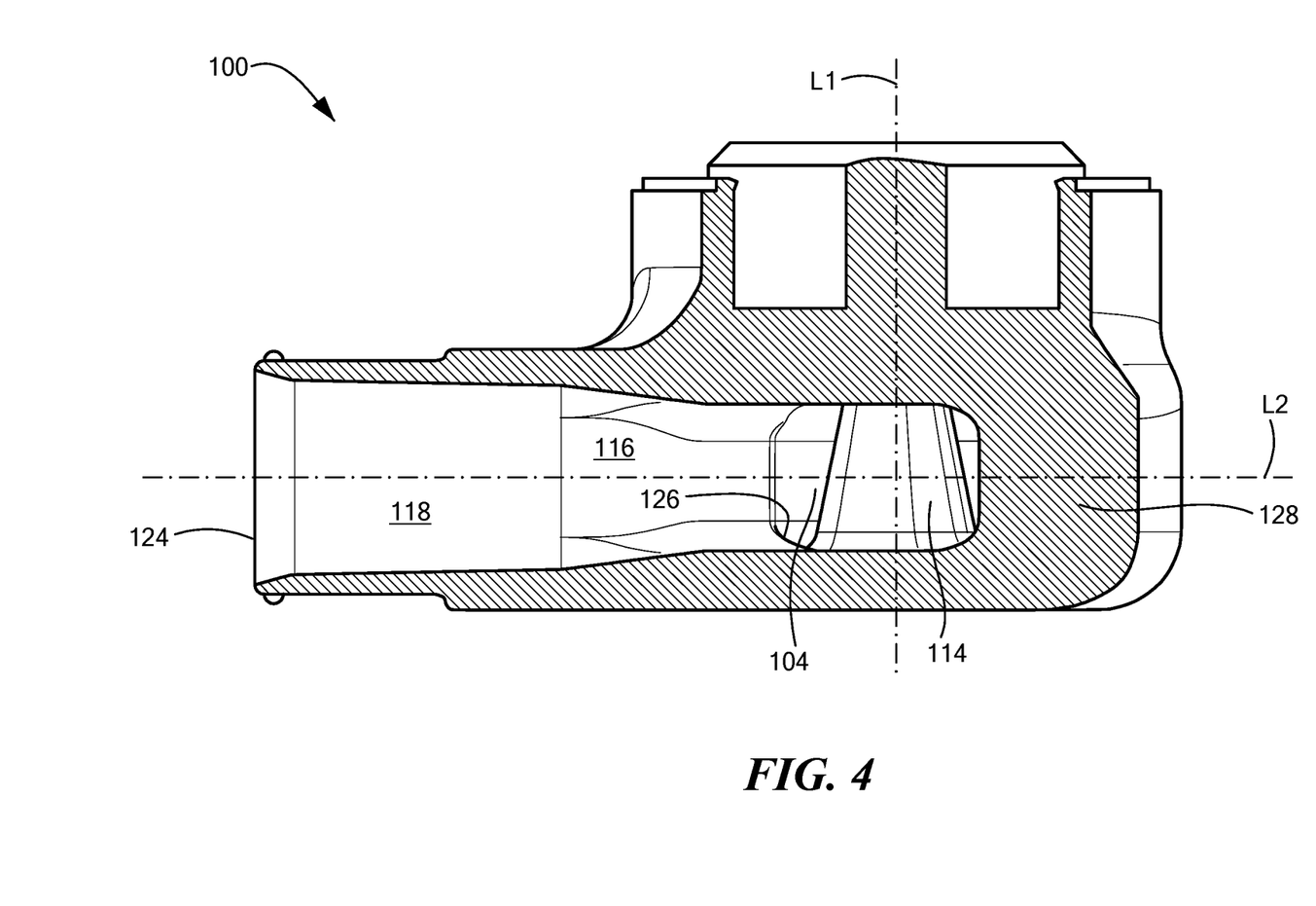
FIG. 4 is a cross-sectional view along line A-- in FIG. 2.
Figure 5:
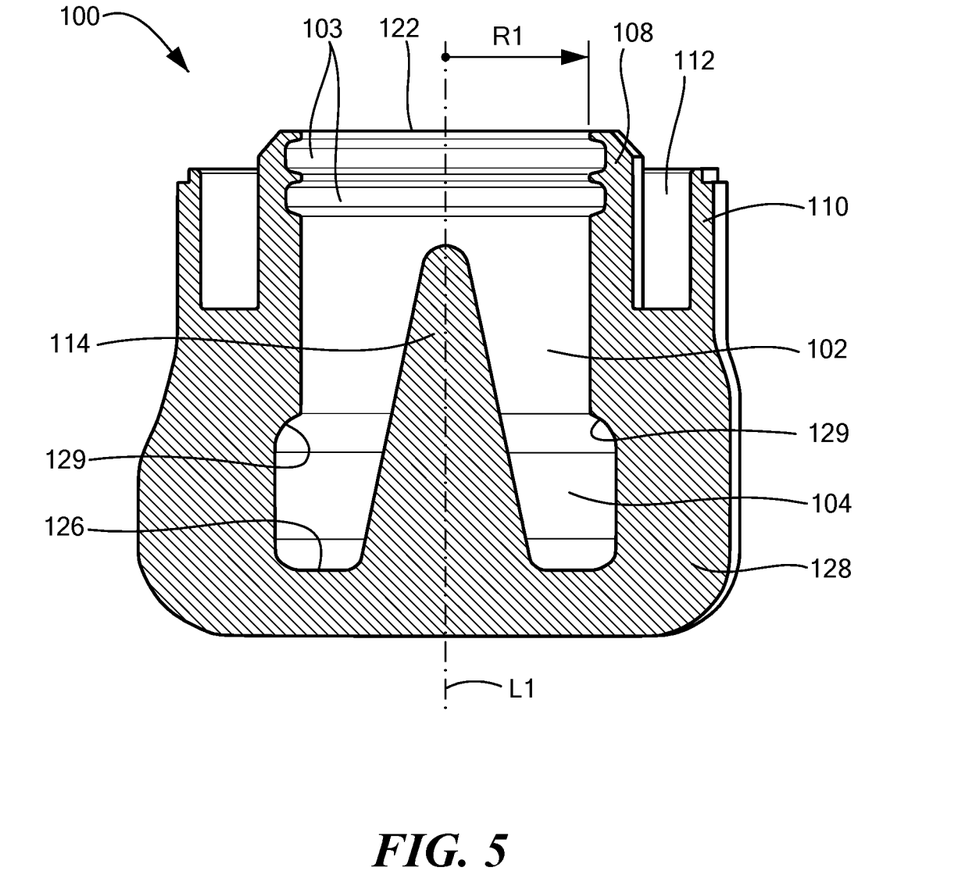
FIG. 5 is a cross-sectional view along line B-- in FIG. 2.
Figure 7:
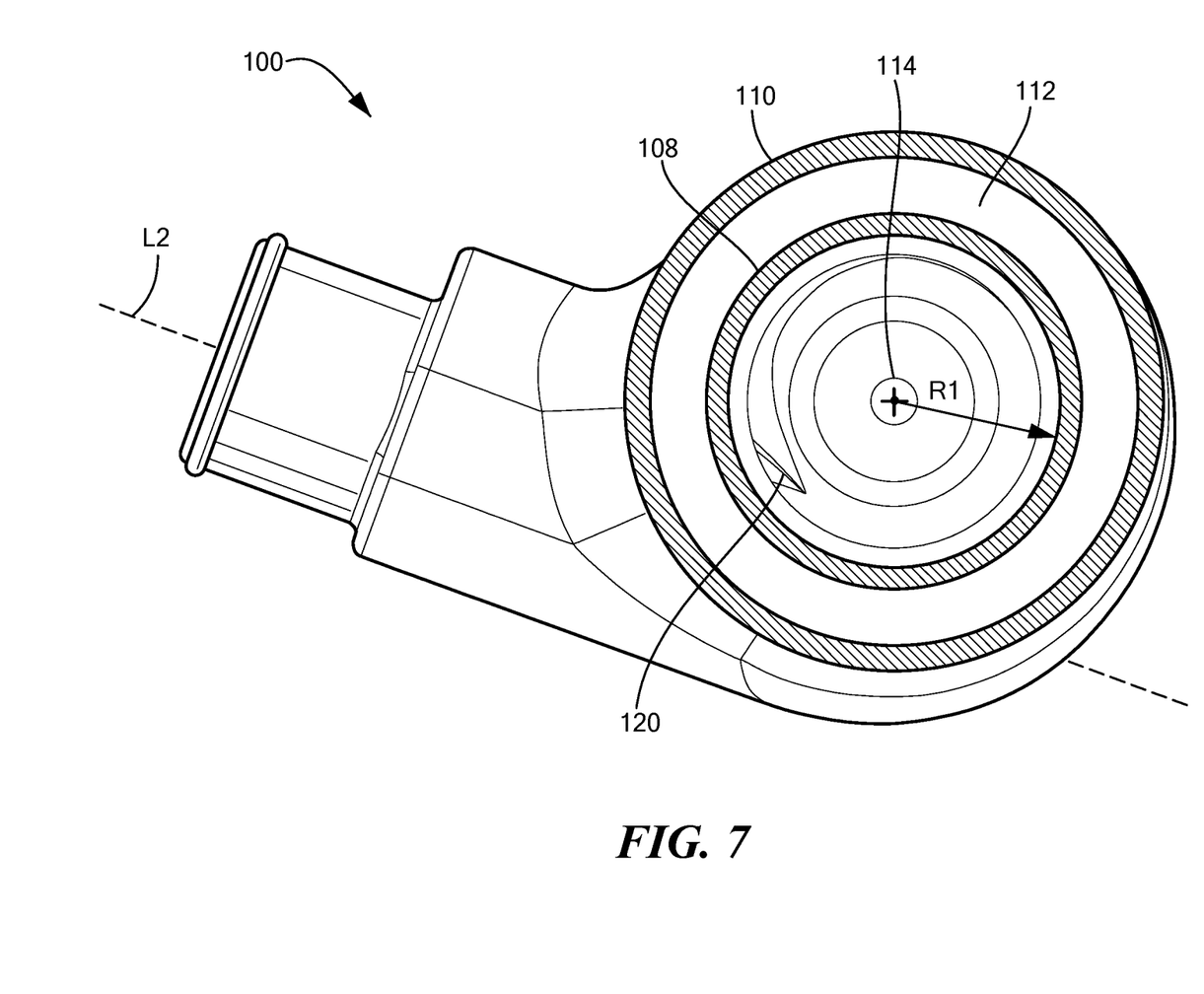
FIG. 7 is a cross-sectional view along line D-- in FIG. 3.

As best seen in FIG. 3 and FIG. 5, the body includes an inner wall 108 which defines an upstream portion of inlet chamber 102 and an inlet port 122 to receive the fluid being pumped at the upstream end of inlet chamber 102. In one configuration, the inlet chamber 102 is substantially cylindrical in shape with a radius R1 measured from the first axis L1 to the inner surface of wall 108. A pair of O-ring grooves 103 (FIG. 5) are provided in the inner surface of wall 108 adjacent inlet port 122. The body also has an external wall 110 spaced radially outward of inner wall 108 and extending around axis L1 so that the inner and outer walls define an annular space 112 (FIG. 7). As discussed below, annular space 112 may be used to house other pump components and/or may facilitate in attaching pump casing 102 to other pump components.

Figure 6:
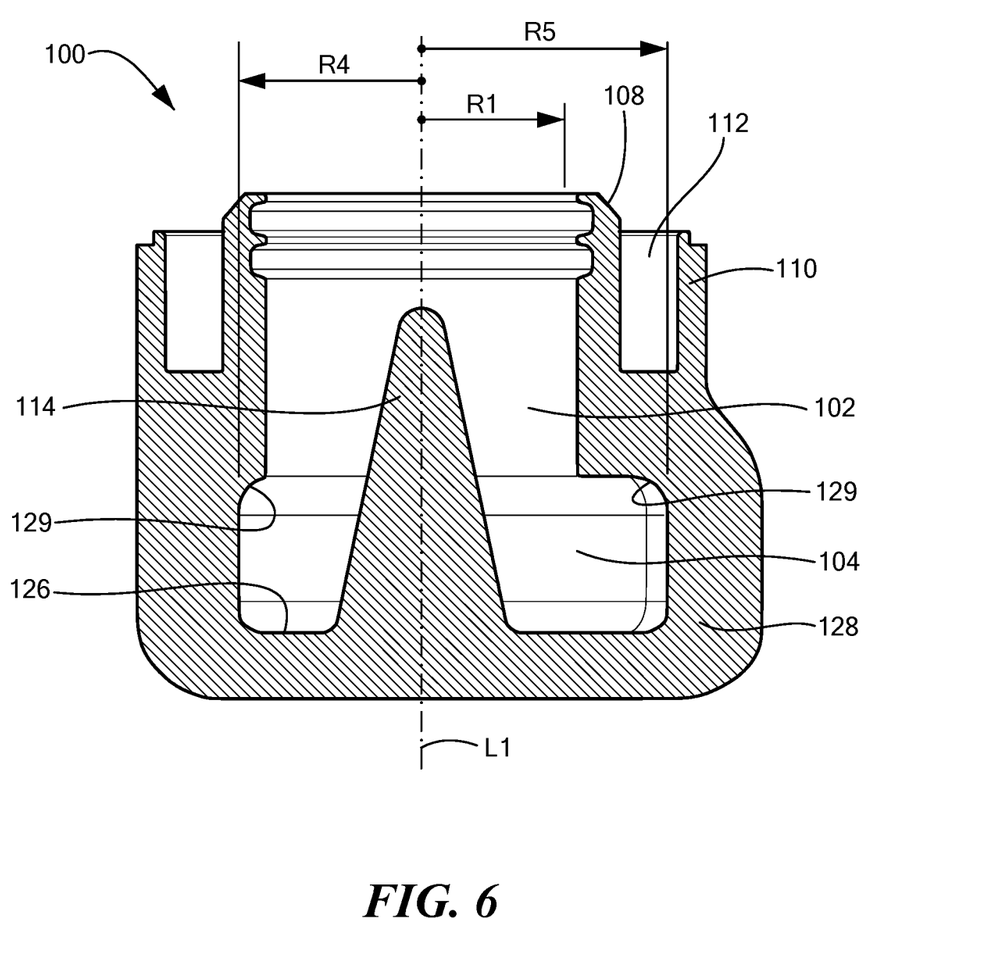
FIG. 6 is a cross-sectional view along line C-- in FIG. 2.
Figure 8:
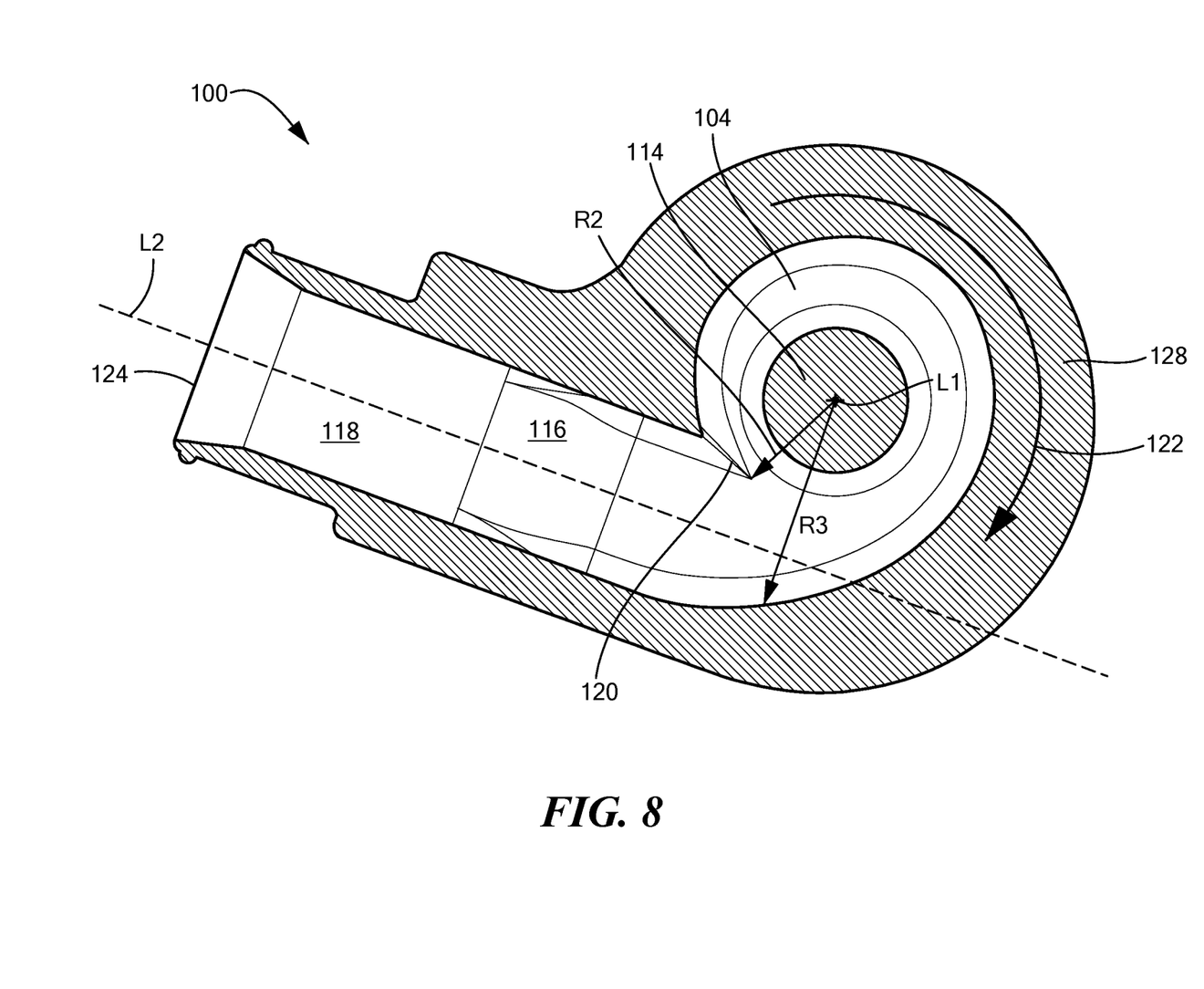
FIG. 8 is a cross-sectional view along line E-- in FIG. 3.

Transition chamber 104 is located downstream of inlet chamber 104. The body includes a wall 128 (FIGS. 5, 6, and 8) extending circumferentially around axis L1 and defining the radial extent of transition chamber 104. As best seem in FIG. 8, transition chamber 104 provides a scroll-shaped flow path. Stated another way, the radius of transition chamber 104 measured from the axis L1 to the inner surface of wall 104 varies in the circumferential direction. The minimum radius R2 is disposed at a tongue 120 located at the entrance to outlet 106. The radius increases progressively in the forward circumferential direction indicated by arrow 122 in FIG. 8 to a maximum radius R3 adjacent to tongue 120 (FIG. 8). As shown in FIG. 6, radius R5 is greater than radius R4. The scroll-shaped flow path is designed to vary the cross-sectional area of the flow path, whereby the most constricted area (at minimum radius R2) is located at tongue 120, and the maximum cross-sectional area (at maximum radius R3) is located at an azimuth angle of approximately 360 degrees in the forward circumferential direction indicated by direction arrow 122 in FIG. 8. The forward circumferential direction corresponds to the direction of flow of the pumped blood during operation. The increasing cross-sectional area in the direction of flow ensures that the static pressure remains constant, which minimizes radial thrust on the pump impeller. The cross-sectional area of the scroll-shaped flow path of the present embodiment is configured based on achieving a constant mean velocity (CMV), other embodiments may utilize other methods including utilizing a constant angular momentum (CAM) method to design the scroll-shaped flow channel. In this embodiment, minor radius R2 of transition chamber 104 is slightly larger than radius R1 of inlet chamber 102, whereas the maximum radius R3 is substantially greater than R1. Thus, the body defines a step 129 with a surface facing in the downstream direction (toward the bottom of the drawing in FIGS. 5 and 6) at the juncture of the inlet chamber 102 and the transition chamber 104.

The body further includes a base wall 126 defining the end surface of transition chamber 104. This end surface is generally planar and perpendicular to the axis L1 of the inlet chamber. A post 114 projects upstream from base wall 126, through the transition chamber 104 and into inlet chamber 102. Post 114 is in the form of a body of revolution around axis L1, with progressively increasing radius in the downstream direction, toward wall 126. In the particular embodiment depicted, post 114 is substantially conical, with a rounded tip at its upstream end. As best appreciated with reference to FIGS. 5 and 6, the end surface defined by wall 126, the step 129 and circumferential wall 128 impart a substantially rectangular cross-sectional shape to the peripheral portions of the transition chamber.

The body further defines a tubular outlet 106 (FIGS. 2, 4 and 8) communicating with the transition chamber. The tubular outlet includes a segment 116 having a generally rectangular cross-sectional shape extending from the juncture of the outlet and the transition chamber, and a segment 118 of generally circular cross-sectional shape extending from segment 118. The cross-sectional area of segment 118 may be larger than the cross-sectional area of segment 116 to decrease the discharge velocity. Tongue 120 (FIG. 8) represents the edge formed at the intersection of the scroll-shaped profile of transition chamber 104 with the tubular outlet 106. Flow below the tongue is directed back to transition chamber 104, whereas flow above the tongue is forced into the outlet 106.

Figure 9A:
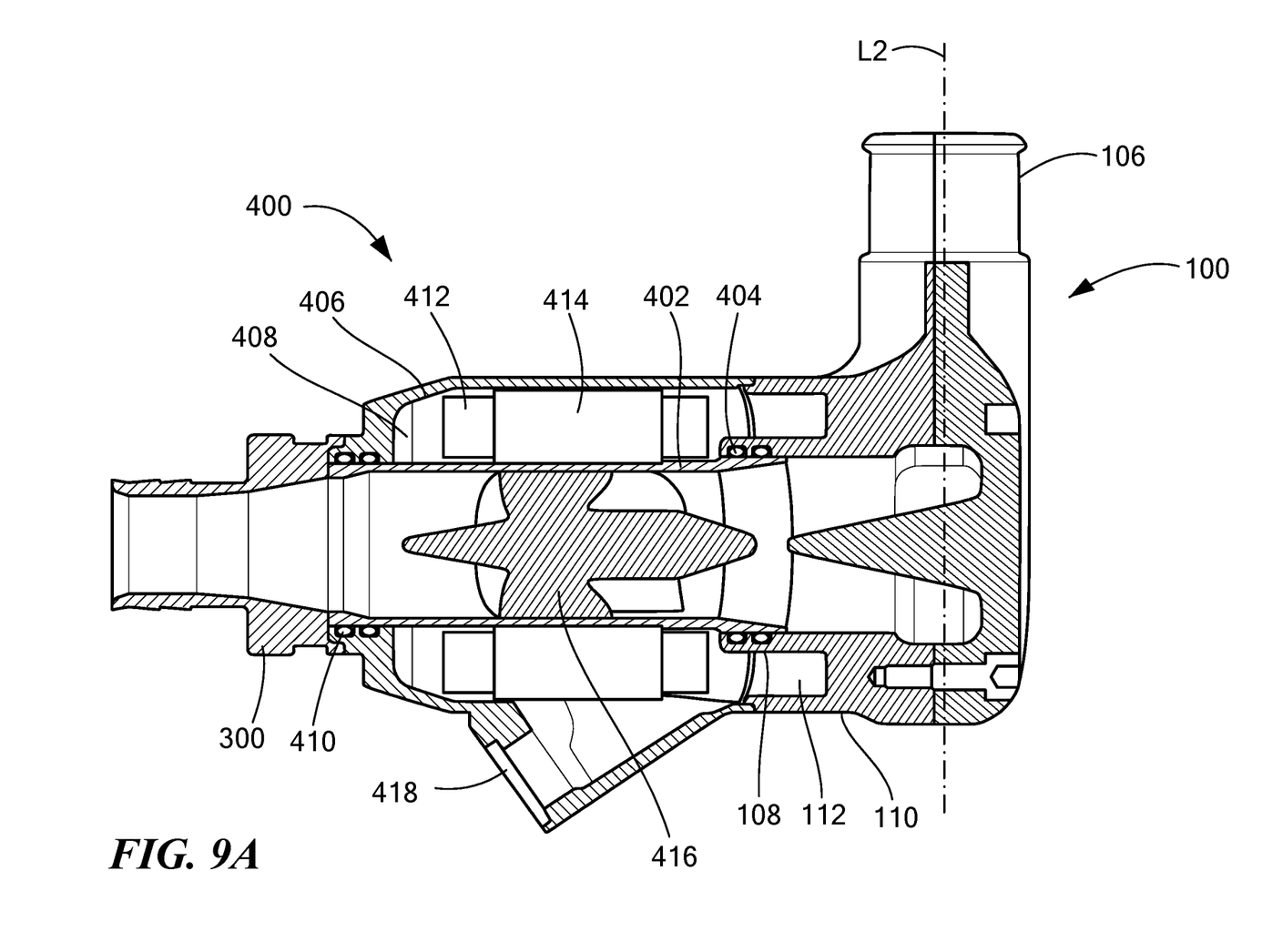
FIG. 9A is a cross-sectional view of a mechanical circulatory support device including the pump casing of FIG. 1.
Figure 9B:
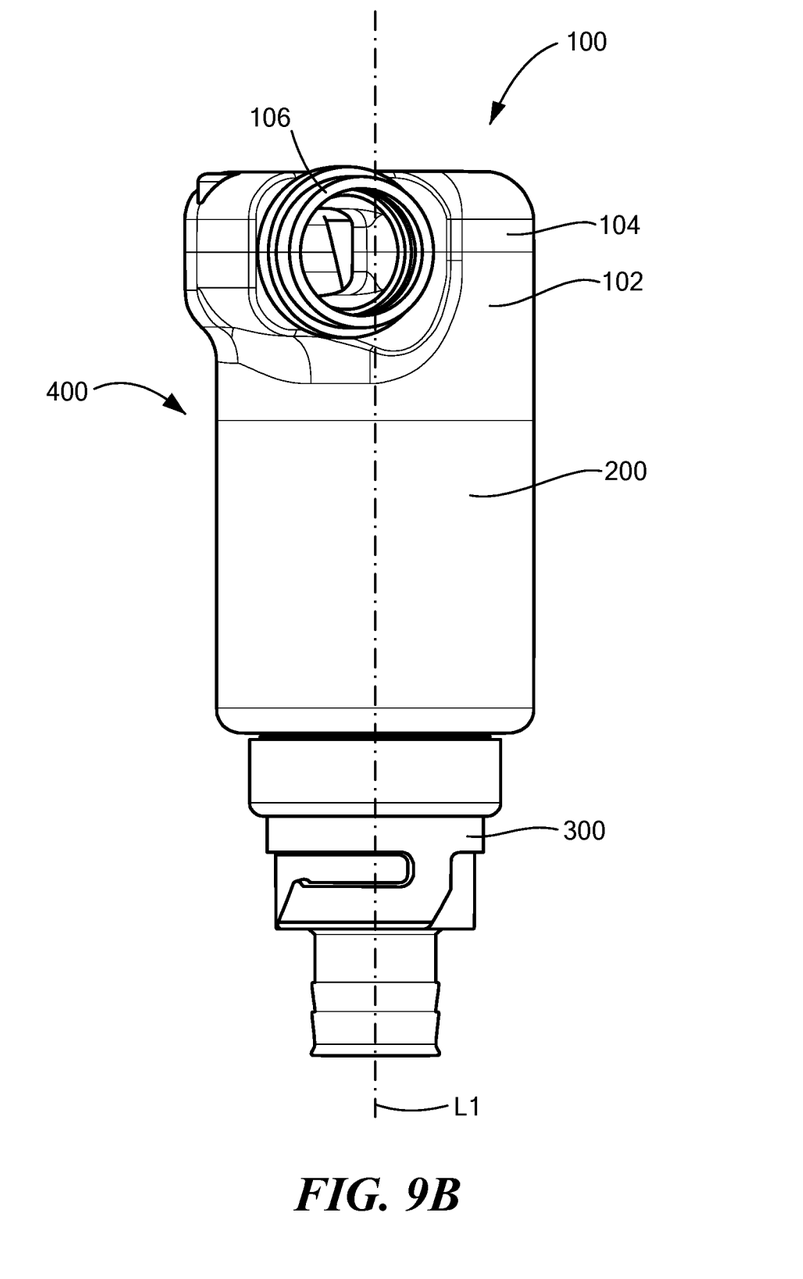
FIG. 9B is an elevational view of the mechanical circulatory support device of FIG. 9A.

FIGS. 9A and 9B show an MCSD incorporating the pump casing 100 discussed above in connection with FIGS. 1-8.

The components of MCSD 400 may be generally as disclosed in U.S. Pat. Nos. 7,972,122; 8,007,254; and 8,419,609, the disclosures of which are hereby incorporated by reference herein. MCSD 400 may include a tubular inner housing 402 connected to the upstream opening 122 of casing 100, and sealed to the inner wall 108 by O-rings 402. An inlet fitting 300 is connected to an upstream end of inner housing 402. The inlet fitting 300 may be removable to allow for insertion and placement of a rotor within the inner housing 402 as more fully disclosed in U.S. Patent Application No. 62/270,189; the disclosure of which is hereby incorporated by reference herein.

A generally cylindrical, hollow outer housing 408 surrounds inner housing 402. The outer housing is spaced from the inner housing so that the inner and outer housings cooperatively define an annular space 408 between them. An upstream end of outer housing 406 is sealed to the outside of inner housing 402 by seals such as O-rings 410. The downstream end of the outer housing is sealingly connected to the outer wall 110 of casing 100. For example, the outer wall 110 may be welded or glued to outer housing 406, or resilient seals such as O-rings (not shown) may be provided between these elements. The space 112 defined by outer wall 110 and the inner wall 108 of the casing communicates with the space 408 within outer housing 406. A set of electrical coils 412 and a ferromagnetic stator frame 414 are disposed within space 408. Electrical wiring (not shown) connected to coils 412 is also disposed within space 408. This wiring is connected to a cable, commonly referred to as a "driveline" (not shown) which extends through a port 418 in outer housing 406. This port is closed by an appropriate seal (not shown), so that the spaces 406 and 112 are sealed from the environment outside of the outer housing. Additional electrical and electronic components (not shown) also may be disposed within space 408, within space 112, or both. Spaces 406 and 112 are also isolated from the blood flowing through the pump in operation. A magnetic rotor 416 is disposed within inner housing 402.

In operation, the MCSD is connected to a patient's circulatory system. For example, the inlet fitting 300 may be connected to a ventricle of the patient's heart, whereas the outlet 106 of casing 100 may be connected to an artery such as to the aorta. The MCSD may be implanted within the patient's body. Rotor 416 is suspended within inner housing 402, out of contact with the walls of the housing, by hydrodynamic bearings (not shown) incorporated in the rotor. Alternating currents applied to the coils created a rotating magnetic field which drives rotor 416 in rotation. The spinning rotor forces blood downstream, towards casing 100.

Pump casing 100 shown in this embodiment may be fabricated as a single monolithic or unitary piece utilizing an additive manufacturing process. As used in this disclosure, the term "additive manufacturing" refers to a process in which successive layers of material are formed to create an object. Typically, a digital three-dimensional design data file is created and converted into two-dimensional patterns, each representing a single layer to be formed. Additive manufacturing techniques include, by way of example, fused deposition modeling and inkjet printing, in which a material is selectively deposited to form each layer; stereolithography, in which a photopolymer is selectively cured to form each layer; and powder bed techniques in which a metal or polymer powder is selectively sintered; Suitable biocompatible material, including medical-grade stereolithography resins may be used to fabricate pump casing 100 by stereolithography.

In the embodiment discussed above, the pump casing bounds the space 406 and 112 housing the electrical and electronic components of the pump, such as coils 414 (FIG. 9). This space is protected from entry of moisture. For example, where the pump is implanted in the body of the patient, the outer wall 110 of the casing desirably has a water vapor transmission rate low enough to limit the moisture permeation into the space during the expected lifetime of the pump to an amount which will not cause unacceptable moisture damage to the electrical and electronic components housed in the space. Where the pump is intended to be a temporary implant for short-term applications on the order of days, weeks or months, the water vapor transmission rate may be higher than a permanent MCSD. In these instances, the pump casing 100 may be fabricated by material with relatively higher permeability to moisture than the material typically used to fabricate permanent MCSDs. Some materials found to be suitable for the dual purposes of stereolithographic fabrication and providing the required level of permeability in a temporary MCSDs include Somos ProtoGen™ 18420 and WaterShed® XC. Although these polymer resins may not provide the permeability protection or durability of a permanent MCSD, these temporary MCSDs provide an inexpensive and temporary alternative. Where the MCSD is intended as a permanent or semi-permanent implant, with an expected lifetime of several years, materials such as metals having even lower permeability can be used. Other additive manufacturing processes such as a shape metal deposition process using an electron beam gun or a laser may be used in conjunction with powdered metal, metal alloys or other composite material.

A monolithic pump casing fabricated by stereolithography may not require material removal, but instead may only require a cleaning process such as vapor polishing before use. As used in this disclosure, a "monolithic" element, such as the body of the pump casing, is a unitary piece of material. Typically, a monolithic element is of uniform composition throughout. However, the composition of the material may vary as, for example, if the composition of the material used during additive manufacturing is varied during deposition of the various layers. Also, a monolithic element optionally may include one or more coatings overlying and conforming to the unitary piece, which are structurally supported by the unitary piece as, for example, coatings formed by plating or vapor deposition.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

What is claimed is:
1. A blood pump casing, comprising:
   a unitary body defining:
      an inlet chamber extending along a first axis and having a first radius perpendicular to the first axis;

a transition chamber connected to the inlet chamber and having a wall extending in a circumferential direction around the first axis, the wall having a major radius and a minor radius from the first axis, the major radius being greater than the first radius;

a post extending from the transition chamber into the inlet chamber along the first axis, the post progressively tapering in the direction around the first axis toward the inlet chamber; and an outlet connected to the transition chamber and extending along a second axis transverse to the first axis.

2. The pump casing of claim 1, wherein the body includes a polymer.

3. The pump casing of claim 1, wherein the minor radius is equal to or greater than the first radius.

4. The pump casing of claim 1, wherein the post is conical.

5. The pump casing of claim 1, wherein the outlet includes an enclosed channel having a first segment with a substantially rectangular cross-section transverse to the second axis in communication with the transition chamber, and a second segment with a substantially circular cross-section transverse to the second axis in communication with the first segment.

6. The pump casing of claim 1, wherein the first axis is perpendicular to the second axis.

7. The pump casing of claim 1, wherein the body includes an inner first wall surrounding the inlet chamber over at least a portion of the axial extent of the inlet chamber and an outer second wall surrounding the first wall, the first and second walls defining an annular space.

8. The pump casing of claim 1, wherein the inlet chamber is cylindrical.

9. A mechanical circulatory support device, comprising:
a unitary body defining:
an inlet chamber extending along a first axis and having a first radius perpendicular to the first axis;
a transition chamber connected to the inlet chamber and having a wall extending in a circumferential direction around the first axis, the wall having a major radius and a minor radius from the first axis, the major radius being greater than the first radius;
a post extending from the transition chamber into the inlet chamber along the first axis, the post progressively tapering in the direction around the first axis toward the inlet chamber;
an outlet connected to the transition chamber and extending along a second axis transverse to the first axis;
a housing connected to the inlet chamber; and
a rotor disposed within the housing and configured to impel blood into the inlet chamber.

10. The device of claim 9, wherein the post is conical.

11. The device of claim 9, wherein the outlet includes an enclosed channel having a first segment with a substantially rectangular cross-section transverse to the second axis in communication with the transition chamber, and a second segment with a substantially circular cross-section transverse to the second axis in communication with the first segment.

12. The device of claim 9, wherein the first axis is perpendicular to the second axis.

13. The device of claim 9, wherein the body includes an inner first wall surrounding the inlet chamber over at least a portion of the axial extent of the inlet chamber and an outer second wall surrounding the first wall, the first and second walls defining an annular space.

14. The device of claim 9, wherein the inlet chamber is cylindrical.

15. A method of fabricating a blood pump casing, comprising:
forming the body of the blood pump casing by an additive manufacturing process, the body of the casing being unitary and defining:
an inlet chamber extending along a first axis and having a first radius perpendicular to the first axis;
a transition chamber connected to the inlet chamber and having a wall extending in a circumferential direction around the first axis, the wall having a major radius and a minor radius from the first axis, the major radius being greater than the first radius;
a post extending from the transition chamber into the inlet chamber along the first axis, the post progressively tapering in the direction around the first axis toward the inlet chamber; and
an outlet connected to the transition chamber and extending along a second axis transverse to the first axis.

16. The method of claim 15, wherein the additive manufacturing process includes stereolithography.

17. The method of claim 15, wherein the body of the casing is made of a resin polymer.

18. The method of claim 15, wherein the additive manufacturing process includes fused deposition modeling.

19. The method of claim 15, wherein the additive manufacturing process includes inkjet printing.

20. The method of claim 15, wherein the additive manufacturing process includes powder bed techniques.

* * * * *